United States Patent
Savaides et al.

(10) Patent No.: US 8,367,049 B2
(45) Date of Patent: Feb. 5, 2013

(54) METHOD AND COMPOSITION FOR REDUCING MALODOR IN PERMANENTLY WAVED HAIR

(75) Inventors: Andrew Savaides, Norwalk, CT (US); Rushi Tasker, Trumbull, CT (US)

(73) Assignee: Zotos International, Inc., Darien, CT (US)

( * ) Notice: Subject to any disclaimer, the term of this patent is extended or adjusted under 35 U.S.C. 154(b) by 1150 days.

(21) Appl. No.: 12/006,628

(22) Filed: Jan. 3, 2008

(65) Prior Publication Data

US 2009/0175816 A1    Jul. 9, 2009

(51) Int. Cl.
*A61Q 5/04*    (2006.01)

(52) U.S. Cl. .................... 424/70.2; 424/70.5; 424/70.51

(58) Field of Classification Search .......... None
See application file for complete search history.

(56) References Cited

U.S. PATENT DOCUMENTS

| 4,115,549 | A | | 9/1978 | Scott ............................... 424/71 |
| 4,898,899 | A | | 2/1990 | Isobe .............................. 524/90 |
| 5,122,418 | A | | 6/1992 | Nakane et al. ................ 424/401 |
| 5,929,513 | A | | 7/1999 | Asano et al. .................. 257/675 |
| 6,024,949 | A | * | 2/2000 | Rose ........................... 424/70.2 |
| 2007/0226918 | A1 | * | 10/2007 | Tagawa ............................ 8/407 |

* cited by examiner

*Primary Examiner* — Jyothsna Venkat
(74) *Attorney, Agent, or Firm* — Ware, Fressola, Van Der Sluys & Adolphson LLP

(57) ABSTRACT

By formulating permanent wave compositions with chlorophyll derivatives of water soluble alkaline divalent cations selected from the group consisting of magnesium, manganese, calcium, copper, and zinc, an easily employed malodor reducing composition is achieved for use with conventional reducing agents employed for permanently waving hair. In accordance with the present invention, chlorophyll derivative compositions soluble in propylene glycol and glycerol are employed in pre-treatments, waving lotions, or as additives to the waving lotions using various different reducing agents salts and esters of TGA, TLA, Cysteine, Cysteamine, and Bisulfite.

8 Claims, No Drawings

METHOD AND COMPOSITION FOR REDUCING MALODOR IN PERMANENTLY WAVED HAIR

TECHNICAL FIELD

This invention relates to the art of permanently waving hair, and more particularly, to treatments for reducing malodor in the hair resulting from the permanent waving operation.

BACKGROUND

The present invention relates to treatments for reducing the perm odor in hair produced during the permanent wave operation. Perm odors have been found to exist due to the use of hair reducing agents such Thioglycolic Acid, Thiolactic Acid, GTG, Cysteine, Cysteamine, Bisulfite or other product compounds that are entrapped into the porous structure of hair. The higher the porosity of hair the higher the binding affinity of the chemical compounds with hair or the higher the level of the odoriferous residues. Other factors that affect the binding affinity are molecular size, net change of reducing agent, electro-static charge of hair and the pH of the waving lotion.

Impurities, volatile mercaptans and other by-products that are formed from complex reactions of the reducing or oxidizing agents with hair are also responsible for the post permanent malodor.

The profile, duration and intensity of the perm odor appears to be dependent on the concentration, reducing agent type used and pH of the waving lotion. Another factor in the perm odor is the odor intensity of the reducing agent. Waving lotions prepared with Cysteine and Bisulfite are less odoriferous than Ammonium Thioglycolate (ATG) and Glyceryl Thioglycolate (GTG). However, all of these agents produce offensive odors.

There are no specific reaction mechanisms for the formation of the odoriferous residues in hair during the operation from the different type of reducing agents. However the perm odor in hair from the different reducing agents or perm products is easily differentiated by the human nose.

The present invention involves the reduction of permanent wave odors formed during and after the perm operation of hair permed with the conventional, well-known reducing agents. Although the intensity and type of the malodor varies depending upon the agent employed, such post-perm malodor in hair is referred or described by individuals as "corn chips", "burned pop corn" or "wet dog" or "cat urine". The intensity of the post-perm malodor is also amplified in cigarette smokers and the body chemistry of individuals.

The post-perm malodor resulting from Cysteamine permanent wave products is not affected by shampooing and it persists in hair for many weeks. The malodor is not noticeable in dry hair but appears to be strong and is released upon water contact. The malodor is continuously being released upon rewetting of the hair.

Therefore, it is a principal object of the present invention to provide a hair treatment composition for reducing the odor in hair caused from a permanent wave operation which is long lasting and is easily applied to the hair during the permanent wave operation or subsequent thereto.

Another object of the present invention is to provide a hair treatment composition having the characteristic features described above which is retained in the hair fibers and avoids removal or dilution by normal hair shampooing or washing.

Another object of the present invention is to provide a hair treatment composition having the characteristic features described above which possesses a unique combination of fragrances that are retained by the hair fibers and effectively render any malodor to be more pleasant.

Another object of the present invention is to provide a hair treatment composition having the characteristic features described above which is capable of reducing, masking, and/or eliminating permanent wave malodor which occurs due to the re-wetting of hair fibers after a permanent wave operation.

Other and more specific objects will in part be obvious and will in part appear hereinafter.

DETAILED DISCLOSURE

By employing the present invention, all of the difficulties and drawbacks found in the prior art have been overcome and an easily employed malodor reducing composition has been achieved for use with conventional reducing agents employed for permanently waving hair. In the following detailed disclosure, the preferred embodiment of the malodor reducing composition of the present invention is fully detailed. However, variations and alterations can be made in the formulations detailed herein without departing from the scope of this invention. Consequently, it is to be understood that the following disclosure is provided for fully detailing the preferred embodiment of this invention, while not intending that the scope of this invention should be limited thereto.

In accordance with the present invention, it has been found that the malodor typically produced during the waving process for permanently waving hair is substantially reduced by formulating permanent wave compositions with chlorophyll derivatives of water soluble alkaline divalent cations selected from the group consisting of magnesium, manganese, calcium, copper, and zinc. In accordance with the present invention, chlorophyll derivative compositions soluble in propylene glycol and glycerol are employed in pre-treatments, waving lotions, or as additives to the waving lotions using various reducing agents salts and esters of TGA, TLA, Cysteine, Cysteamine, and Bisulfite.

It has been found that the aqueous/glycol chlorophyll compositions of the present invention may be used as pre-treatments prior to the keratin reducing step or during the keratin reducing step and/or the neutralizing step. Regardless of which application process is employed, excellent deodorization effects are realized. In addition, it has also been found that the chlorophyll derivatives of the present invention reduced the post perm malodor when used as post-treatments, either as a rinse-off or a leave-in product, such as conditioners, shampoos, or refreshing sprays.

It has also been found that the chlorophyll concentration employed in the composition for obtaining the desired results preferably ranges from between about 0.000100% to 0.0080% by weight, based upon the weight of the entire composition. In addition, it has been found that the preferred composition of the chlorophyll concentration comprises about 0.005 percent by weight, based upon the weight of the entire composition.

Furthermore, although the present invention can be employed at various stages during the permanent waving of hair, as detailed above, the present invention is preferably employed as an additive into the wave lotion which is added thereto immediately prior to use. In addition, divalent metal magnesium or copper chlorophyll is preferably employed.

BEST MODE FOR CARRYING OUT THE INVENTION

In order to substantiate the efficacy of the malodor reducing composition of the present invention, the following examples are presented. In the following disclosure, the universal applicability of this invention is fully detailed, along with the ability of the composition of the present invention to substantially reduce and/or eliminate malodor associated with permanently waved hair. It is to be understood, however, that these examples are intended as a teaching of the best mode for carrying out the present invention and are not intended to limit, in any manner, the breath of this discovery.

In order to demonstrate the efficacy of the present invention, a permanent waving lotion was prepared incorporating various concentrations of chlorophyll derivatives in accordance with the present invention. In Table I, three alternate formulations are fully detailed, with Composition 1 being prepared without any chlorophyll derivatives and, thereby, representing the control formulation. In addition, in Table II, the results of a hydrogen sulfide head space test performed on each of the compositions of Table I are provided.

TABLE I

| | % Wt/Wt | | |
|---|---|---|---|
| Composition | 1 | 2 | 3 |
| Water, Deonized | 69.35 | 69.35 | 69.35 |
| Thioglycolic acid | 10.80 | 10.80 | 10.80 |
| Diammonium Dithiodiglycolate | 2.00 | 2.00 | 2.00 |
| Ammonium Bicarbonate | 2.00 | 2.00 | 2.00 |
| Ammonium Hydroxide | 0.53 | 0.53 | 0.53 |
| Gycerine | 0.50 | 0.50 | 0.50 |
| Non Ionic Surfactant | 1.20 | 1.20 | 1.20 |
| Fragrance | 0.40 | 0.40 | 0.40 |
| Chlorophyll Derivatives | 0.00 | 0.0001 | 0.0003 |

TABLE II

| | Hydrogen Sulfide (ppm) | | |
|---|---|---|---|
| #of Strokes (50 cc) | Composition1 | Composition 2 | Composition 3 |
| 1 | 34 | 23 | 12 |
| 2 | 63 | 45 | 28 |
| 3 | 85 | 65 | 43 |
| 4 | 110 | 87 | 58 |

In providing the results detailed in Table 2, the head space of each wave lotion composition was analyzed with a hydrogen sulfide sensor tube, and the results obtained from four successive 50 cc head space analysis tests are provided. As is evident from these results, the average levels of hydrogen sulfide for Composition 1, the control composition, is 29.33 ppm, while the average level for Composition 2 is 21.25 ppm, with Composition 3 having an average level of 14.5 ppm.

As is evident from this test, the head space analysis of Compositions 2 and 3 show a remarkable effect on the suppression of malodor associated with hydrogen sulfide release rate. In this regard, more than a 50% reduction is obtained with Composition 3.

This substantial reduction in malodor has been confirmed in salon testing with waving lotions containing TGA, such as Compositions 1, 2, and 3, Glyceryl Thioglycolate, Cysteamine, Cysteamine/TGA and TGA exothermic. In numerous tests conducted in the salon, the malodor reduction has been overwhelmingly noticed by both test subjects and hair stylists. In addition, olfactory evaluation panels have also been conducted and produced similar results.

As discussed above, in the preferred embodiment of the present invention, chlorophyll derivatives are added directly into the waving lotion to produce concentrations ranging between about 0.0001% and 0.008% by weight based upon the weight of the entire composition, with 0.005% being preferred. In addition, the chlorophyll derivatives are preferably added into the waving lotion just prior to use.

In this regard, it has been found that the preferred chlorophyll composition is prepared separately and added to the waving lotion just prior to use of the waving lotion. In Table 3, a preferred formulation for the chlorophyll composition additive of the present invention is provided.

TABLE III

| Preferred Chlorophyll Composition | |
|---|---|
| | % W/W |
| Glycerine | 75.00 |
| Propylene Glycol | 24.95 |
| Chlorophyll Derivatives | 0.05 |

In order to provide further evidence of the broad applicability and highly effective malodor reduction achieved by the present invention, twelve additional waving lotion compositions were prepared and tested. In Tables IV and V, these additional compositions are fully detailed. Furthermore, as is evident from a review of Tables IV and V, in each of these compositions, the preferred chlorophyll formulation provided in Table III was employed, with 10% by weight based upon the weight of the entire composition being used in each formulation.

TABLE IV

| Waving Lotion Compositions | | | | | | |
|---|---|---|---|---|---|---|
| | W/W % | | | | | |
| | 5 | 6 | 7* | 8** | 9*** | 10 |
| Water, Deionized | 60.00 | 70.69 | 47.59 | 71.97 | 80.5 | .83 |
| Ammonium Thioglycolate 60% | 18.00 | 13.67 | 33.60 | 3.33 | — | 5.42 |
| L-Cysteine Hydrochloride | — | — | — | — | — | 11.65 |
| Diammonium Dithiodiglycolate 40% | 5.00 | 3.00 | — | 7.20 | 3.00 | — |
| Polyquaternium-28 | 1.00 | — | — | — | — | 1.00 |
| Quaternium-75 | — | — | 2.50 | — | — | — |
| Polyquaternium-10 | 0.065 | 0.065 | 0.065 | 0.10 | 0.10 | — |
| Ammonium Hydroxide, 28% | 1.96 | 0.25 | 1.00 | 4.50 | 3.40 | 2.00 |
| Ammonium Bicarbonate | 2.00 | 2.00 | 2.50 | — | — | 2.00 |
| Trisodium EDTA | — | — | 0.10 | — | — | — |
| Glycerine | 0.50 | 5.00 | — | — | — | 0.50 |
| Solubilizer | 1.20 | 0.60 | 1.20 | 1.20 | 1.20 | 1.20 |
| Fragrance | 0.40 | 0.20 | 0.40 | 0.40 | 0.40 | .40 |

TABLE IV-continued

Waving Lotion Compositions

| | W/W % | | | | | |
|---|---|---|---|---|---|---|
| | 5 | 6 | 7* | 8** | 9*** | 10 |
| Sodium Borate | — | — | — | 1.00 | 1.00 | — |
| Preservative | — | — | — | 0.40 | 0.40 | — |
| Chlorophyll Composition (Table III) | 10 | 10 | 10 | 10 | 10 | 10 |
| Wave Lotion Additive | — | — | 18.72 | 21.57 | 25.20 | |

*= 81.28% of composition 7 is mixed with 18.72% of 4% Hydrogen Peroxide
**= 78.43% of composition 8 is mixed with 21.57% of 80% Glyceryl Thioglycolate (GMT)
***= 74.80% of composition 9 is mixed with 25.20% of 80% Glyceryl Thioglycolate (GMT)

TABLE V

WAVING LOTION COMPOSITIONS

| | W/W % | | | | | |
|---|---|---|---|---|---|---|
| | 11 | 12 | 13+ | 14 | 15 | 16 |
| Water, Deionized | 71.70 | 68.80 | 52.38 | 63.96 | 69.20 | 49.46 |
| Cysteamine HCl 75% | 11.00 | 13.00 | 26.60 | 6.67 | — | — |
| Ethanolamine Thioglycolate 40% | — | — | — | 15.00 | — | — |
| Ammonium Thiolactate 60% | — | — | — | — | 15.00 | — |
| Ammonium Bisulfite 45% | — | — | — | — | — | 23.0 |
| Isopropyl Alcohol | — | — | — | — | — | 3.00 |
| Glycerol | — | 0.5 | 0.5 | 0.5 | 0.5 | 1.00 |
| Ammonium Hydroxide, 28% | 2.50 | 1.00 | 5.92 | — | 1.00 | 4.20 |
| Ammonium Bicarbonate | 2.00 | 2.00 | — | — | 2.0 | — |
| Solubilizer | 2.10 | 2.10 | 3.75 | 1.20 | 2.10 | 1.44 |
| Fragrance | 0.70 | 0.70 | 1.25 | 0.40 | 0.70 | 0.40 |
| Urea | — | — | — | 0.20 | — | 7.50 |
| Disodium EDTA | — | — | — | 0.20 | — | — |
| Monoethanolamine | — | — | — | 2.07 | — | — |
| Chlorophyll Composition (Table III) | 10 | 10 | 10 | 10 | 10 | 10 |
| Wave Lotion Additive | — | — | 17.60 | — | — | — |

+= 82.39% of composition 12 is mixed with 17.60% of 4% Hydrogen Peroxide

In conducting this product evaluation, each of the formulations detailed above were prepared freshly by mixing the chlorophyll composition of Table III with the waving lotion, followed with the application of the waving lotion on pre-wrapped hair. The hair was then processed in accordance with the directions for the particular hair type being tested.

The odor evaluation and effective odor reduction was evaluated by hair stylists employing four full head models for each composition and using the olfactory method. The evaluation was carried out for the malodor release during the following operational steps: (1) processing, (2) after water rinsing, (3) at the end of the operation or neutralization step, and (4) after one or two weeks of the initial operation. The evaluation results are provided in Table VI, along with the interpretation or meaning of the rating scale employed therein.

TABLE VI

ODOR RATING

| Composition | Processing | Water Rinsing | Neutralization | After 1 week |
|---|---|---|---|---|
| 5 | 4.25 | 4.00 | 4.50 | 4.50 |
| 6 | 4.0 | 4.00 | 4.50 | 4.65 |
| 7 | 3.75 | 4.00 | 4.00 | 4.75 |
| 8 | 4.50 | 4.50 | 4.50 | 4.75 |
| 9 | 4.00 | 4.60 | 4.60 | 4.75 |
| 10 | 4.25 | 4.50 | 4.50 | 4.25 |
| 11 | 4.25 | 4.25 | 4.50 | 4.50 |
| 12 | 4.25 | 4.50 | 4.25 | 4.30 |
| 13 | 4.50 | 4.50 | 4.65 | 4.50 |
| 14 | 4.25 | 4.50 | 4.25 | 4.50 |
| 15 | 4.00 | 4.65 | 4.50 | 4.50 |
| 16 | 4.25 | 4.35 | 4.50 | 4.60 |

TABLE VII

Pretreatment Chlorophyll Composition

| | Wt/Wt % |
|---|---|
| Deonized Water | 96.17 |
| PEG-40 Hydrogenated Castor Oil | 1.35 |
| PPG-26-Buteth 26 | 1.35 |
| PEG-2 Oleammonium Chloride | 0.20 |
| Glycerol | 0.20 |
| Propylene Glycol | 0.10 |
| Fragrance | 0.40 |
| Citric Acid | 0.13 |
| Chlorophyll Derivatives | 0.005 |
| Simethicone | 0.10 |

Finally, although the composition of the present invention is preferably employed directly in the waving lotion, the chlorophyll composition can also be used as a pre-treatment or post-treatment, as discussed above. In this regard, Table VII fully details a preferred chlorophyll composition in accordance with the present invention which can be used as pre-treatment for application to the hair prior to the use of a waving lotion.

TABLE VIII

Post-treatment Chlorophyll Composition

| | W/W |
|---|---|
| Deonized Water | 96.65 |
| Vegetable Protein | 1.00 |
| Solubilizer/Surfactant | 0.70 |
| Fragrance | 0.70 |
| PEG-2 Oleammonium Chloride and propylene Glycol | 0.30 |
| Sodium PCA | 0.20 |
| Glycerine | 0.20 |
| Disodium EDTA | 0.10 |
| Chlorophyll Derivatives | 0.005 |
| Phosphoric Acid | 0.12 |
| Citric Acid QS to pH 3.7 | |

The post-treatment composition Table VIII is applied on damp permed hair for 3 minutes, followed with water rinsing.

It will thus be seen that the objects set forth above, among those made apparent from the preceding description, are efficiently entertained and, since certain changes may be made in carrying out the above method and in the compositions set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure up by Letters Patent is:

1. An odor-reducing treatment for application to hair as part of a permanent wave process, the treatment comprising the application to hair of a permanent wave formulation, wherein the permanent wave formulation comprises a chlorophyll composition comprising chlorophyll derivatives selected from the group consisting of magnesium chlorophyll, manganese chlorophyll, calcium chlorophyll, copper chlorophyll and zinc chlorophyll, and
   wherein the concentration of the chlorophyll derivatives in the permanent wave formulation is between about 0.0001% and 0.008% by weight based upon the weight of the entire permanent wave formulation.

2. The odor-reducing treatment defined in claim 1, wherein the chlorophyll composition further comprises propylene glycol and glycerol.

3. The odor-reducing treatment defined in claim 1, wherein the permanent wave formulation is further defined as being employed during the permanent wave process as a pre-treatment, a waving lotion, a post-treatment, or a neutralizing solution.

4. The odor-reducing treatment defined in claim 1, wherein the permanent wave formulation is a waving lotion comprising a reducing agent salt and ester selected from the group consisting of thioglycolic acid, thiolactic acid, cysteine and cysteamine.

5. The odor-reducing treatment defined in claim 1, wherein the concentration of chlorophyll derivatives in the permanent wave formulation is further defined as comprising about 0.005% by weight based upon the weight of the entire permanent wave formulation.

6. The odor-reducing treatment defined in claim 1, wherein the concentration of the chlorophyll composition in the permanent wave formulation is about 10% by weight based upon the weight of the entire permanent wave formulation.

7. The odor-reducing treatment defined in claim 1, wherein the permanent wave formulation comprises a waving lotion, and wherein the chlorophyll composition is mixed into the waving lotion immediately prior to the application of the waving lotion to hair.

8. An odor-reducing treatment for application to hair as part of a permanent wave process, the treatment comprising the application to hair of a permanent wave formulation, wherein the permanent wave formulation comprises a chlorophyll composition comprising chlorophyll derivatives selected from the group consisting of magnesium chlorophyll, manganese chlorophyll, calcium chlorophyll, copper chlorophyll and zinc chlorophyll, wherein the chlorophyll composition is further defined as comprising about 0.05% of the chlorophyll derivatives by weight based upon the weight of the entire chlorophyll composition, about 75% glycerine by weight based upon the weight of the entire chlorophyll composition, and about 24.95% propylene glycol by weight based upon the weight of the entire chlorophyll composition.

* * * * *

UNITED STATES PATENT AND TRADEMARK OFFICE
CERTIFICATE OF CORRECTION

| | | |
|---|---|---|
| PATENT NO. | : 8,367,049 B2 | Page 1 of 1 |
| APPLICATION NO. | : 12/006628 | |
| DATED | : February 5, 2013 | |
| INVENTOR(S) | : Savaides et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1219 days.

Signed and Sealed this
Second Day of December, 2014

Michelle K. Lee
*Deputy Director of the United States Patent and Trademark Office*